(12) United States Patent
Nanni

(10) Patent No.: US 12,004,942 B2
(45) Date of Patent: Jun. 11, 2024

(54) MESH OR MEMBRANE COVERING BASED ON BIOLOGICAL OR BIOSYNTHETIC MATERIAL FOR PROSTHESIS, PROVIDED WITH FIXING SYSTEM FOR FIXING TO THE SAME PROSTHESIS, AND CORRESPONDING MANUFACTURING PROCESS THEREOF

(71) Applicants: Flavio Nanni, Preci (IT); Nello Cara, Rome (IT); Federica Gulizia, Rome (IT); Valter Varano, Rome (IT)

(72) Inventor: Flavio Nanni, Preci (IT)

(73) Assignees: Flavio Nanni, Preci (IT); Nello Cara, Rome (IT); Federia Gulizia, Rome (IT); Valter Varano, Rome (IT)

(*) Notice: Subject to any disclaimer, the term of this patent is extended or adjusted under 35 U.S.C. 154(b) by 692 days.

(21) Appl. No.: 17/019,424

(22) Filed: Sep. 14, 2020

(65) Prior Publication Data

US 2020/0405473 A1    Dec. 31, 2020

Related U.S. Application Data

(63) Continuation-in-part of application No. PCT/IT2019/050054, filed on Mar. 13, 2019.

(51) Int. Cl.
*A61F 2/12*    (2006.01)
*A61L 2/00*    (2006.01)
(Continued)

(52) U.S. Cl.
CPC .............. *A61F 2/12* (2013.01); *A61L 2/0023* (2013.01); *A61L 2/0035* (2013.01); *A61L 2/007* (2013.01);
(Continued)

(58) Field of Classification Search
CPC ................ A61F 2/12; A61F 2210/0004; A61F 2220/0025; A61F 2220/0075;
(Continued)

(56) References Cited

U.S. PATENT DOCUMENTS 4,298,998 A    11/1981 Naficy
4,772,285 A    9/1988 Ksander et al.
(Continued)

FOREIGN PATENT DOCUMENTS

BR    102017007853 A2 *    10/2018
CN    103393482    11/2013
(Continued)

OTHER PUBLICATIONS

International Search Report and the Written Opinion dated Oct. 8, 2019 From the International Searching Authority Re. Application No. PCT/IT2019/050054. (18 Pages).
(Continued)

*Primary Examiner* — Suzette J Gherbi

(57) ABSTRACT

The present invention relates to a mesh or membrane covering (2) based on biological material, for example collagen, or biosynthetic material for prostheses (1), in particular for a breast prosthesis (1), said prosthesis (1) having a rear surface that, when applied, is faced towards the person on whom (1) is applied, said covering (2) being characterized in that it provides a fixing system (4; 3) for fixing to said prosthesis (1), said fixing system providing a plurality of teeth or petals (4) or outer perimeter edge foldable on said rear surface of the prosthesis (1) by means (5). The invention further relates to a method for fixing said covering to a prosthesis, a prosthesis comprising said covering and a process for making said covering.

32 Claims, 11 Drawing Sheets

(51) Int. Cl.
*A61L 27/36* (2006.01)
*A61L 101/44* (2006.01)

(52) U.S. Cl.
CPC ........... *A61L 2/0094* (2013.01); *A61L 27/362* (2013.01); *A61L 27/3625* (2013.01); *A61F 2210/0004* (2013.01); *A61F 2220/0025* (2013.01); *A61F 2220/0075* (2013.01); *A61F 2230/0006* (2013.01); *A61F 2230/0008* (2013.01); *A61L 2101/44* (2020.08); *A61L 2202/21* (2013.01)

(58) Field of Classification Search
CPC ..... A61F 2230/0006; A61F 2230/0008; A61L 2/007; A61L 27/362; A61L 27/3625
See application file for complete search history.

(56) References Cited

U.S. PATENT DOCUMENTS

| | | | |
|---|---|---|---|
| 4,840,629 A | 6/1989 | Bostos | |
| 5,356,432 A * | 10/1994 | Rutkow | A61F 2/0063 623/23.72 |
| 6,113,634 A | 9/2000 | Weber-Unger et al. | |
| 6,146,418 A | 11/2000 | Berman | |
| 6,210,439 B1 | 4/2001 | Firmin et al. | |
| 10,028,826 B2 * | 7/2018 | Yohanan | A61F 2/2436 |
| 10,405,969 B2 | 9/2019 | Bertoli et al. | |
| 11,083,564 B2 * | 8/2021 | Gryskiewicz | A61F 2/12 |
| 11,090,146 B1 * | 8/2021 | Young | A61L 27/54 |
| 11,642,207 B2 * | 5/2023 | Young | A61L 27/54 623/8 |
| 2002/0042658 A1 | 4/2002 | Tyagi et al. | |
| 2003/0036803 A1 | 2/2003 | McGhan | |
| 2006/0030939 A1 | 2/2006 | Frank | |
| 2007/0088434 A1 | 4/2007 | Frank | |
| 2008/0241212 A1 | 10/2008 | Moses et al. | |
| 2008/0281419 A1 | 11/2008 | Matheny et al. | |
| 2009/0082864 A1 * | 3/2009 | Chen | A61F 2/12 623/8 |
| 2009/0125107 A1 | 5/2009 | Maxwell et al. | |
| 2009/0149953 A1 | 6/2009 | Schuessler et al. | |
| 2009/0198332 A1 | 8/2009 | Becker | |
| 2009/0198333 A1 | 8/2009 | Becker | |
| 2010/0010627 A1 | 1/2010 | Matheny | |
| 2010/0023029 A1 * | 1/2010 | Young | A61F 2/0063 606/151 |
| 2010/0028396 A1 | 2/2010 | Ward et al. | |
| 2011/0035004 A1 | 2/2011 | Maxwell | |
| 2011/0082545 A1 | 4/2011 | Freund | |
| 2011/0238179 A1 * | 9/2011 | Laurencin | A61F 2/08 623/13.19 |
| 2011/0288639 A1 | 11/2011 | Trilokekar et al. | |
| 2012/0041555 A1 | 2/2012 | Manesis et al. | |
| 2012/0053690 A1 | 3/2012 | Frank | |
| 2012/0123535 A1 | 5/2012 | Alejandro | |
| 2012/0143329 A1 | 6/2012 | Kim | |
| 2012/0143330 A1 | 6/2012 | Linares | |
| 2012/0150204 A1 | 6/2012 | Mortarino | |
| 2012/0226352 A1 | 6/2012 | Becker | |
| 2013/0261745 A1 | 10/2013 | Van Epps | |
| 2013/0282033 A1 | 10/2013 | Caballero | |
| 2013/0304098 A1 * | 11/2013 | Mortarino | A61F 2/12 606/151 |
| 2014/0088700 A1 | 3/2014 | Mortarino et al. | |
| 2014/0155917 A1 | 6/2014 | Horton | |
| 2014/0236210 A1 | 8/2014 | Payne et al. | |
| 2015/0223928 A1 | 8/2015 | Limem et al. | |
| 2015/0351891 A1 | 12/2015 | Moses et al. | |
| 2016/0199173 A1 * | 7/2016 | Liu | A61F 2/12 435/395 |
| 2016/0250016 A1 | 9/2016 | Bertoli | |
| 2016/0331504 A1 | 11/2016 | Wang et al. | |
| 2017/0340437 A1 | 11/2017 | Bowley et al. | |
| 2018/0055624 A1 | 3/2018 | Barere et al. | |
| 2019/0336273 A1 | 11/2019 | Bertoli et al. | |
| 2020/0100892 A1 * | 4/2020 | Limem | A61L 27/18 |
| 2020/0113667 A1 * | 4/2020 | Eggers | A61F 2/0105 |
| 2020/0390944 A1 * | 12/2020 | Williams | A61B 17/80 |
| 2020/0405473 A1 * | 12/2020 | Nanni | A61L 27/3625 |
| 2021/0153997 A1 * | 5/2021 | Limem | A61F 2/0077 |

FOREIGN PATENT DOCUMENTS

| | | |
|---|---|---|
| CN | 105997302 | 10/2016 |
| EP | 0230672 | 8/1987 |
| EP | 0322194 | 6/1989 |
| EP | 2524670 | 11/2012 |
| EP | 2569021 | 1/2017 |
| EP | 3081189 | 7/2018 |
| EP | 2571543 | 12/2018 |
| EP | 2903563 | 7/2020 |
| EP | 3400900 | 8/2020 |
| EP | 2802288 | 9/2020 |
| FR | 2682284 | 4/1993 |
| FR | 2746298 | 9/1997 |
| FR | 3025999 | 3/2016 |
| IT | 2012A00148 | 7/2012 |
| IT | 0000278047 | 5/2014 |
| IT | 0000283625 | 10/2017 |
| IT | 102016000012465 | 10/2018 |
| IT | 102016000041094 | 10/2018 |
| JP | 6-292716 | 10/1994 |
| KR | 10-0947468 | 3/2019 |
| WO | WO 95/07666 | 3/1995 |
| WO | WO 97/04722 | 2/1997 |
| WO | WO 2005/094694 | 10/2005 |
| WO | WO 2006/117622 | 11/2006 |
| WO | WO 2007/004214 | 1/2007 |
| WO | WO 2007/075394 | 7/2007 |
| WO | WO 2008/121816 | 10/2008 |
| WO | WO 2009/001293 | 12/2008 |
| WO | WO 2009/039371 | 3/2009 |
| WO | WO 2009/039373 | 3/2009 |
| WO | WO 2009/049910 | 4/2009 |
| WO | WO 2009/050706 | 4/2009 |
| WO | WO 2009/065013 | 5/2009 |
| WO | WO 2011/008496 | 1/2011 |
| WO | WO 2011/011394 | 1/2011 |
| WO | WO 2011/097292 | 8/2011 |
| WO | WO 2011/112626 | 9/2011 |
| WO | WO 2011/140382 | 11/2011 |
| WO | WO 2011/143206 | 11/2011 |
| WO | WO 2012/122215 | 9/2012 |
| WO | WO 2013/106556 | 7/2013 |
| WO | WO 2014/041577 | 3/2014 |
| WO | WO 2014/047617 | 3/2014 |
| WO | WO 2015/006737 | 1/2015 |
| WO | WO 2016/172094 | 10/2016 |
| WO | WO 2016/186803 | 11/2016 |
| WO | WO 2017/183055 | 10/2017 |
| WO | WO 2018/195476 | 10/2018 |
| WO | WO 2019/094861 | 5/2019 |
| WO | WO 2019/157048 | 8/2019 |
| WO | WO 2019/175911 | 9/2019 |
| WO | WO-2019175911 A2 * | 9/2019 ........... A61F 2/0077 |

OTHER PUBLICATIONS

Rapporto di Ricerca e Opinione Scritta [Search Report and Written Opinion] dated Nov. 26, 2018 From the Ministerio Dello Sviluppo Economico, Direzione Generale Sviluppo Produttivo e Competitivita, Ufficio Italiano Brevetti e Marchi Re. Application No. IT201800003509. (13 Pages).

Communication Under Rule 71(3) EPC Dated Feb. 24, 2022 From the European Patent Office Re. Application No. 19716586.3. (41 Pages).

Consultation by Telephone With the Applicant Dated Oct. 12, 2021 From the European Patent Office Re. Application No. 19716586.3. (3 Pages).

Rapporto di Ricerca e Opinione Scritta [Search Report and Written Opinion] Dated Oct. 4, 2020 From the Ministerio Dello Sviluppo

(56) References Cited

OTHER PUBLICATIONS

Economico, Direzione Generale Sviluppo Produttivo e Competitivita, Ufficio Italiano Brevetti e Marchi Re. Application No. IT202000004183. (15 Pages).

Rapporto di Ricerca e Opinione Scritta [Search Report and Written Opinion] dated Feb. 10, 2021 From the Ministerio Dello Sviluppo Economico, Direzione Generale Sviluppo Produttivo e Competitivita, Ufficio Italiano Brevetti e Marchi Re. Application No. IT202000010930. (12 Pages).

Casella et al. "TiLoop® Bra Mesh Used for Immediate Breast Reconstruction: Comparison of Retropectoral and Subcutaneous Implant Placement in A Prospective Single-Institution Series", European Journal of Plastic Surgery, 37(11): 599-604, Published Online Aug. 3, 2014.

Nahabedian "Current Approaches to Prepectoral Breast Reconstruction", Plasctic and Reconstructive Surgery, 142(4): 871-880, Oct. 2018.

PFM Medical "Plastic Surgery: TiLOOP® Bra", PFM Medical, Product Description, PUE1012, 2 P., Jun. 2014.

Sigalove "Options in Acellular Dermal Matrix-Device Assembly", Plastic and Reconstructive Surgey, 140(6S Prepectoral Breast Reconstruction): 39S-42S, December Supplement 2017.

Ter Louw et al. "Prepectoral Breast Reconstruction", Plastic and Reconstructive Surgery, 140(5S Advances in Breast Reconstruction): 51S-59S , November Supplement 2017.

\* cited by examiner

MESH OR MEMBRANE COVERING BASED ON BIOLOGICAL OR BIOSYNTHETIC MATERIAL FOR PROSTHESIS, PROVIDED WITH FIXING SYSTEM FOR FIXING TO THE SAME PROSTHESIS, AND CORRESPONDING MANUFACTURING PROCESS THEREOF

RELATED APPLICATIONS

This application is a Continuation-in-Part (CIP) of PCT Patent Application No. PCT/IT2019/050054 having International filing date of Mar. 13, 2019, which claims the benefit of priority of Italian Patent Applications Nos. 102018000003509 filed on Mar. 13, 2018, and 102018000009810 filed on Oct. 26, 2018. The contents of the above applications are all incorporated by reference as if fully set forth herein in their entirety.

FIELD AND BACKGROUND OF THE INVENTION

The present invention relates to a mesh or membrane covering based on biological or biosynthetic material for prostheses, with fixing system for fixing to the same prosthesis, and corresponding manufacturing process thereof.

The invention further relates to a prosthesis, like for example a silicone breast prosthesis, covered with a mesh or membrane based on biological or biosynthetic material sticking to the silicone surface of the prosthesis.

As is well known, the phenomenon of capsular contracture is a frequent complication that occurs following a surgical intervention to implant a silicone prosthesis, like for example breast prostheses. The prosthesis implant causes a reaction in the organism, called reaction to a foreign body, i.e. defence mechanism of the organism having the purpose of isolating the prosthesis, which represents the foreign body, from the rest of the organism by the formation of a capsule of fibres that encases the prosthesis itself. After the surgical intervention, the capsule consisting of neoformed fibres can contract, causing deformations of the prosthesis that are often so serious as to require further surgical intervention to correct the aesthetic blemish caused by the deformation of the prosthesis.

In order to solve this problem, over the years prostheses covered with medical polyurethane foam have been proposed. Nevertheless, in systems of this type, the phenomenon of capsular contracture, as described in the literature, is merely postponed; the question of the side effects of polyurethane foam is still a matter of debate.

Another method for reducing the risk of capsular contracture consists of wrapping the silicone prosthesis in commercially available collagen meshes. According to this method, the medical operator prepares the prosthesis directly in the operating theatre just before the surgical intervention. The sterile prosthesis and the sterile collagen mesh are extracted from the respective packages thereof, which ensure the sterility thereof and are handled by the medical operator to wrap the prosthesis in the mesh and sew the mesh in such a way that it follows the shape of the prosthesis. The final result is thus entrusted to the dexterity and experience of the medical operator, who may encounter difficulties in covering the prosthesis evenly with the mesh. Further, the step of preparing the prosthesis, in addition to lengthening time in the operating theatre, exposes the prosthesis to the risk of contamination because of the prolonged handling. Another drawback is the risk of compromising the integrity of the prosthesis in the step of stitching the mesh, for example by pricking the prosthesis with the needle. In this case, the prosthesis will have to be replaced with an undamaged prosthesis with a resulting waste of material, increased costs and time in the operating theatre.

Prostheses covered with collagen are also known. Some examples thereof can be found in the patent documents U.S. Pat. No. 4,772,285, US2011/035004, US2012/226352, US2009/198332.

These are prostheses that comprise a silicone portion covered with a mesh or membrane based on biological or biosynthetic material adhering homogeneously and stably to the surface of the prosthesis.

Although these remedies are able to solve some of the above problems, they do not allow a complete solution, because in none of the solutions is an advantageous system disclosed for fixing the covering on the prosthesis, so that the covering may separate from the prosthesis, or not be fixed to the prosthesis stably over time.

United States patent application US 2016/0331504 A1 discloses a covering for breast prostheses that provides a system for fixing to the prosthesis that uses belts adapted to be fixed to the rear surface of the prosthesis. Nevertheless, this fixing system works only in one or two directions that are transverse to one or another, not enabling the prosthesis to be wrapped completely and thus not adhering properly to the surface thereof. Further, this fixing system requires constant handling of the prosthesis-covering assembly, which is strongly advised against by the scientific literature (see, for example: Valdatta L. et al., Hindawi Publishing Corporation, Plastic Surgery International, Vol. 2014, Art. ID 472604, pages 1-10; Israeli R., Plastic and Reconstructive Surgery, Nov. Suppl 2012, Vol. 130, no 5S-2, pages 159S-172S; Rodriguez-Feliz J., Plastic and Reconstructive Surgery, August 2015, Vol. 136, no 2, pages 221-231; Scheflan M., Plastic and Reconstructive Surgery, January 2018, Vol. 141, no 1, pages 1e-10e).

European patent application EP 0 322 194 A1 also relates to a covering for a prosthesis but made of non-reabsorbable PTFE synthetic material. This covering is adapted to create a prosthesis that resists deformation caused by the scar contracture (spherical scar contracture). The purpose is thus to disorganize the scar tissue. Nevertheless, it is not able to protect the cutaneous strip, muscular strip or cutaneous muscle from possible adverse effects caused by contact with the surface of the prosthesis, because the covering is applied as if it were a sock that wraps the prosthesis and is not fixed to the prosthesis, which is able to move freely in relation to the covering. This movement causes continuous jerks (movements) that prevent the covering from neovascularizing because formation of new vessels is interrupted continuously on the membrane covering. Delayed or failed neovascularization slows or inhibits the integration process.

International patent application WO 2013/106556 A2 relates to a covering for prostheses but is however adapted to covering only one portion of the front surface of the prosthesis. Further, this covering is not elastic but rigid, static, does not adhere well to the surface of the prosthesis and, in particular, to prostheses of different formats and dimensions.

United States patent application US 2009/0125107 A1 relates to a covering in dermal material or non bioreabsorbable dermal material for prostheses. This covering is fixed to the prosthesis by sutures, adhesives or appendages on the outer surface of the prosthesis on both the front and the rear face. One drawback of this solution is that it requires a modification to the prosthesis itself. The limit is that the covering is compatible only with prostheses designed for this purpose, not with all those present on the market. Further, the presence of such rigid appendages on the body of the prosthesis can be considered to be a limit because it can cause ischaemia or an inflammatory reaction until the appendages are put at risk of extrusion by the organism.

SUMMARY OF THE INVENTION

In the light of what has been set out above, there is a clear need to be able to have available a method and a mesh or membrane covering based on biological or biosynthetic material for prosthesis, with a secure and permanent fixing system to the prosthesis.

A further aim is to develop a covering that is able to protect the cutaneous strip, muscular strip or cutaneous muscle from possible adverse effects caused by contact with the surface of the prosthesis.

The need is moreover clear to be able to have a process available for making the covering according to the invention.

With the solution according to the present invention, a prosthesis is obtained with a covering that enables the phenomenon of capsular contracture and thus the need to intervene surgically following the implant to be avoided or reduced significantly. The mesh or membrane based on biological or biosynthetic material that wraps the prosthesis and interfaces with the organism is fixed perfectly to the prosthesis, and is able to trigger integration mechanisms for integrating the prosthesis into the organism by induction of neovascularization of the covering in contact with the tissues of the organism. This avoid the formation of an excessive deposit of scar tissue that represents the cause of the phenomenon of the capsular contracture, with the possibility of immediate use of the medical device without any need for handling by the medical operators.

In this manner, the problem of possible contamination of the prosthesis is solved that is due to the handling step and the ensuing problems of risk to the health of the patient.

A possible compromise of the integrity of the prosthesis is moreover avoided and thus allows an enormous financial saving.

In particular, solid adhesion between the prosthesis and the covering according to the present invention with the mesh or the membrane based on biological or biosynthetic material allows better handling during implanting of the prosthesis.

Lastly, the prosthesis according to the present invention enables surgery times to be reduced significantly.

Accordingly, a specific object of the present invention is constituted by a mesh or membrane covering for a prosthesis, in particular for a breast prosthesis, said covering being based on biological material, for example collagen, or biosynthetic material, said prosthesis having a rear surface that, when applied, is faced towards the person on whom is applied, said covering being characterized in that it provides a fixing system for fixing on said prosthesis, said fixing system providing a plurality of teeth or petals, made on a covering, said teeth or petals being configured to be foldable during the industrial manufacturing step, so that when the covering is arranged on said prosthesis said teeth or petals are coupled with said rear surface of the prosthesis by securing means for securing the teeth or petals folded over said prosthesis.

Preferably, according to the invention, said plurality of teeth or petals can be between two and forty-eight, preferably sixteen.

Further, according to the invention, said plurality of teeth or petals can be arranged in spoke fashion on the outer perimeter of said covering.

Still according to the invention, said plurality of teeth or petals can have a length comprised between 5 mm and 50 mm, preferably 20 mm.

Still according to the invention, on at least two or on each tooth or petal a through hole or at least one slot-shaped incision can be obtained, for example single or double, said through hole or at least one slot-shaped incision being adapted to the passage of at least one thread, in particular at least one suture thread.

In particular, according to the invention, each through hole or incision can be arranged in the upper third of the height of the respective tooth or petal.

Further, the object of the present invention is a mesh or membrane covering based on biological material, for example collagen, or biosynthetic material for a prosthesis, in particular for a breast prosthesis, said prosthesis having a rear surface that, when applied, is faced towards the person on whom is applied, said covering being characterized in providing a fixing system for fixing to said prosthesis, said fixing system providing a plurality of holes or incisions obtained at the or on the outer edge of said covering, said holes or incisions being so configured that, when the covering is arranged on said prosthesis, they allow the passage of one or more threads, in particular suture threads to allow the tightening of said outer edge on the rear surface of said prosthesis to be fixed thereto.

Further according to the invention, the diameter of each hole can be comprised between 0.5 mm and 3.0 mm, preferably 1.5 mm.

Preferably according to the invention, said covering can have a mesh portion, in particular at the central part of said covering. More preferably, according to the invention, said mesh portion can have a centrifugal expansion.

In particular, according to the invention, said mesh portion can be obtained by a mesh of wire elements.

Still according to the invention, said covering can be a membrane wherein the mesh portion can have a plurality of notches. Preferably according to the invention, said notches can have a centrifugal expansion with respect to the centre of said covering.

In particular, according to the invention, said notches can be linear notches and can be arranged in spoke fashion with respect to the centre of said covering.

Still according to the invention, said notches can be radial notches and can be arranged on concentric or spiral closed lines, in particular said closed lines can have a polygonal shape.

Further, according to the invention, said notches can be so arranged as to form a plurality of, adjacent and contiguous triangular sections.

Also, according to the invention, said notches can be so arranged as to form a plurality of adjacent triangular sections separated by a uniform area, wherein each uniform area is devoid of notches or cuts or incisions or slits. In particular, each uniform area can connect a central portion of the covering to a peripheral portion of the covering.

Further, according to the invention, the triangular sections can be between three and six triangular sections, being preferably four triangular sections.

Still according to the invention, the length of each of said notches can be comprised between 2 mm to 2 cm.

Preferably according to the invention, the distance between several closed lines can be comprised between 2 mm and 2 cm.

Further according to the invention, the outer perimeter of said covering can have a circular or elliptic or polygonal shape adapted to be inscribed or circumscribed on a circle or an ellipse.

Further, according to the invention, when the outer perimeter of the covering has an elliptic or circular shape, the proportional ratio between the axes of the ellipse can be comprised between 1:1 to 3:1, preferably can be equal to 2:1.6.

In particular, according to the invention, said covering can have a peripheral portion or band made of a full non uniform surface, that surrounds on the perimeter the mesh portion, said peripheral band being devoid of notches or incisions or slits.

Still according to the invention, said peripheral band can have a thickness comprised between 5 mm and 3 cm.

Still according to the invention, said covering can provide a central portion surrounded by said mesh portion, said central portion having a uniform surface free of notches or incisions or slits.

In particular, according to the invention, the diameter of said central portion can vary between 2 cm and 5 cm.

Still according to the invention, said covering can be made exclusively from one or more biopolymers or from a mixture of one or more biopolymers and further ingredients, such as for example elastin.

Still according to the invention, said one or more biopolymers can be chosen between poly-4-hydroxybutyrate or polylactic acid, or a glycolide, lactide and trimethylene carbonate copolymer and a lactide and trimethylene carbonate copolymer.

Further according to the invention, the fibres of each of said copolymers can be co-woven to constitute the mesh covering.

Alternatively, according to the invention, said covering can be made of resorbable and biocompatible material, in particular decellularized biological matrices, more in particular in pericardium, in particular bi-layer or non bi-layer pericardium, or of dermis Further, the object of the present invention is a kit for the covering of a prosthesis, in particular of a breast prosthesis, said kit comprising a covering as disclosed previously, said covering being characterized in that it comprises fixing means for fixing the covering to said prosthesis, wherein said fixing means are a disk, said disk being so configured that when said covering is arranged on said prosthesis said disk is able to cover a folded area of the teeth or petals or of the outer perimeter edge of the covering.

In particular, according to the invention, said disk preferably can be made of smooth or corrugated elastomeric material, covered with polyurethane made of collagen or another medical grade biopolymer, that covers an area of the folded teeth or petals or of the outer perimeter edge, said disk being fixed in position by gluing, vulcanization, self-vulcanization, radiofrequency induction welding or by laser.

Furthermore, a kit according to the invention, can comprise a covering according to the invention and fixing means for fixing said covering to said prosthesis, wherein said fixing means can be one or more threads, in particular suture threads, adapted to pass through said holes or incisions obtained on said teeth or petals or on said perimeter edge.

Still according to the invention, said one or more threads can be inserted through said holes or incisions.

In particular, according to the invention, said one or more threads can be inserted through said holes or incisions so that, when said covering is in use for covering a prosthesis, and said one or more threads are subjected to manual traction, said teeth or petals are synchronously pulled towards the centre of the rear face of the prosthesis, consequently causing the wrapping of the prosthesis by the covering For example, such wrapping of the prosthesis may be obtained with a "purse-string" closure.

Furthermore, according to the invention, said kit may comprise a pair of threads inserted through said holes in an opposite direction to one another, so that their respective ends are coupled on opposite sides of the covering. In particular, said pair of wires can be adapted to be simultaneously subjected to said manual traction.

Further the object of the present invention is a prosthesis having a rear surface and comprising a covering as disclosed previously, said covering being applied to said prosthesis with said plurality of teeth or petals or outer perimeter edge folded and fixed at said rear surface.

Still according to the invention, on said rear surface of said prosthesis a plurality of housings can be provided, corresponding to said teeth or fins in number and shape.

Still according to the invention, said prosthesis can comprise a kit as disclosed previously.

Further, the object of the present invention is a method for fixing the disclosed covering to the disclosed prosthesis, characterized in that it provides the following steps:
    arranging said covering on said prosthesis by folding said teeth or petals or said outer perimeter edge of the covering on the rear surface of said prosthesis.

Still according to the invention, this method can provide the following step:
    fixing said disk to said fins or teeth or petals or to said outer perimeter edge of the covering in position by gluing, vulcanization, self-vulcanization, radiofrequency induction welding or by laser.

Further according to the invention, this method can provide the following step:
    sterilizing said prosthesis by beta or gamma rays, or ethylene oxide, dry heat or hydrogen peroxide plasma.

Still according to the invention, this method can provide the step of:
    fixing said covering to said prosthesis with said one or more threads, in particular suture threads, inserted through said incision holes, or inserting said one or more threads, in particular suture threads, through said holes or incisions, and pulling at least one portion of said threads, causing the tightening of said teeth or petals or outer perimeter edge of said covering on the rear surface of said prosthesis.

Still according to the invention, said method can provide the step of:
    immersing the covering and the prosthesis in a fluid, in particular in a liquid, in particular in a physiological solution.

The invention further relates to a process for making said covering for prostheses, said process providing the steps of:
    making a shell;
    making a counter shell;
    applying a membrane to said shell;
    coupling said counter shell on said shell;
    subjecting the shell-membrane-counter shell assembly to a drying step;
    extracting the shaped membrane.

Preferably, according to the invention, said shell and counter shell can be made by a 3D printer loaded with wire made of material certified for use with foodstuffs and pharmaceuticals.

In particular, said shell and counter shell can be obtained following scanning of the specific prosthesis for which the covering is intended.

Still according to the invention, said shell and counter shell can be made of perforated or non perforated material.

Preferably, according to the invention, said drying step can be achieved by lyophilization.

Still according to the invention, said membrane can be die-cut to measure and preferably with a centrifugal expansion mesh cut and be optionally provided with teeth or petals.

Further, according to the invention, said shell provides a centring device, that passes through a small hole centrally arranged on the membrane and enables centring thereof in the shell, said shell being optionally provided with fins, in a measure and number equal to the number of teeth or petals on the membrane, said fins being provided with hook means, which hook the membrane.

BRIEF DESCRIPTION OF THE SEVERAL VIEWS OF THE DRAWINGS

The present invention will now be described, by way of illustration and not by way of limitation, according to a preferred embodiment thereof, with particular reference to the figures of the appended drawings, wherein.

DESCRIPTION OF SPECIFIC EMBODIMENTS OF THE INVENTION

Referring initially to FIGS. 1-4 of the attached drawings, with the numeric reference 1 a prosthesis is indicated, in particular a breast prosthesis, in particular a prosthesis made of silicone, whereas with the numeric reference 2 the covering according to the invention is indicated, which is made of biological or biosynthetic material, such as for example collagen.

Preferably, the covering 2 according to the invention can be made of reabsorbable and biocompatible material, like for example decellularized biological matrices, in particular bi-layer or non bi-layer pericardium, or dermis. A reabsorbable material is the ability of a given material to be degraded by enzymes once implanted inside the human body.

A biocompatible material is a material that can be metabolized by living organisms without any harmful effect on vital functions. Biocompatibility is a parameter that indicates the harmfulness of a substance for an organism.

Further, said covering 2 can be made exclusively from one or more biopolymers or from a mixture of one or more biopolymers and further ingredients, like for example elastin, adapted to make the elasticity of the covering 2 consistent with the elasticity of the prosthesis 1. Said one or more biopolymers can be chosen from between poly-4-hydroxybutyrate or polylactic acid, or a glycolide, lactide and trimethylene carbonate copolymer and a lactide and trimethylene carbonate copolymer. For example the fibres of each of said copolymers can be co-woven to constitute the mesh covering 2.

Figure 1:
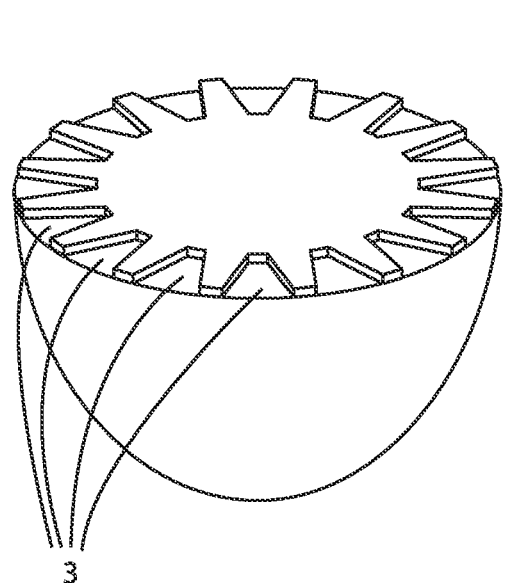
FIG. 1 is a perspective view of an embodiment of a prosthesis according to the invention.

The prosthesis 1 intended to be covered can be produced with a traditional method or by applying to the mould a modification that enables housings 3 (as shown in FIG. 1) to be obtained on the rear face of the prosthesis 1, i.e. the face facing the chest of the patient.

Figure 2:
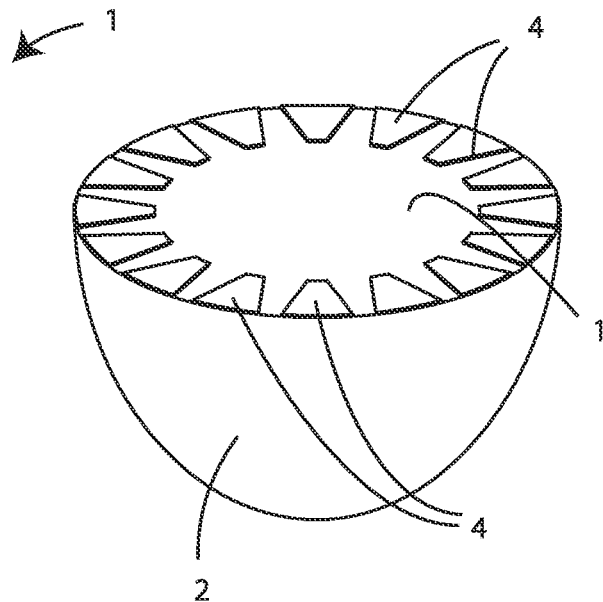
FIG. 2 is a second perspective view of the prosthesis of FIG. 1 with a covering according to the invention.

The covering 2 will have on an outer periphery a plurality of teeth or petals or fins 4 that will couple with the rear portion of the prosthesis 1, or the portion facing the patient, as will be disclosed below, and in the embodiment of FIGS. 1 and 2 in said housings 3. In this text, the fins 4 will be referred to alternatively or equivalently as petals or teeth or fins or flaps.

Figure 4:
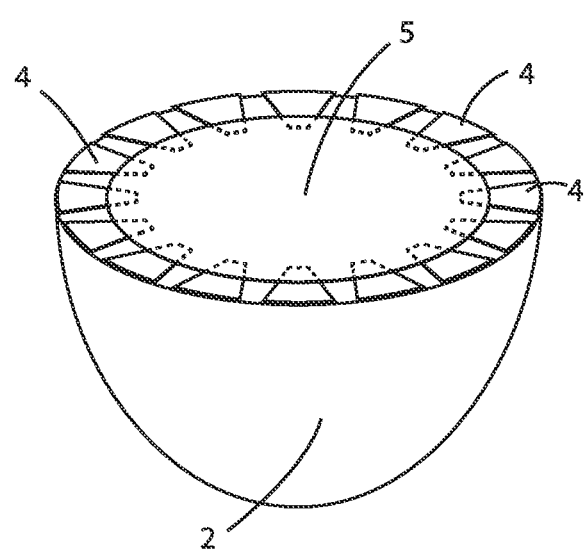
FIG. 4 is a further perspective view of the prosthesis di FIG. 1 with covering according to the invention.
Figure 5:
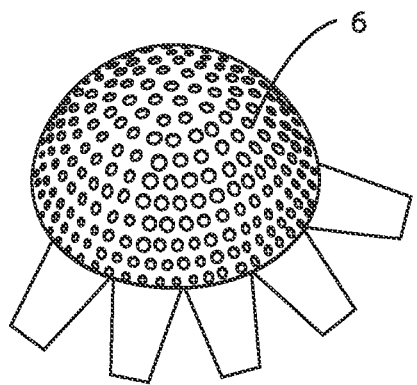
FIGS. 5 and 6 are perspective views of a mould and counter-mould used for the procedure of making the covering according to the invention.
Figure 6:
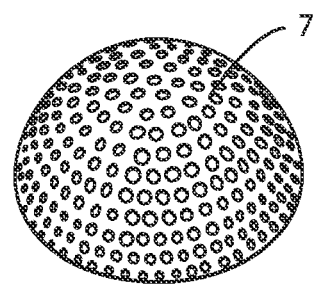
Figure 7A:
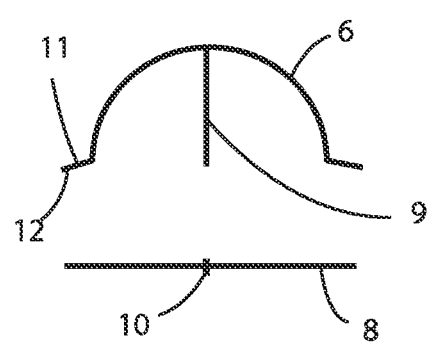
FIGS. 7a and 7b are respectively lateral section views of the mould and counter-mould system according to FIGS. 5 and 6.
Figure 7B:
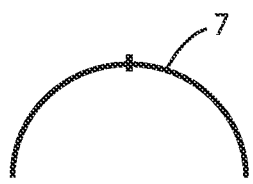
Figure 8A:
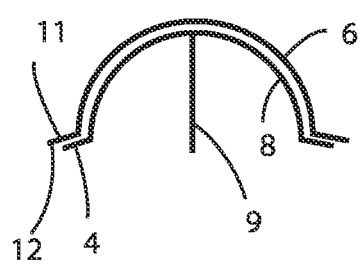
FIGS. 8a and 8b are respectively second lateral section views of the mould and counter-mould system according to FIGS. 5 and 6.
Figure 8B:
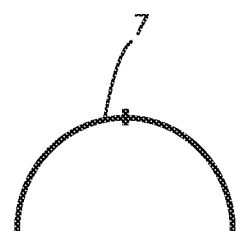
Figure 9:
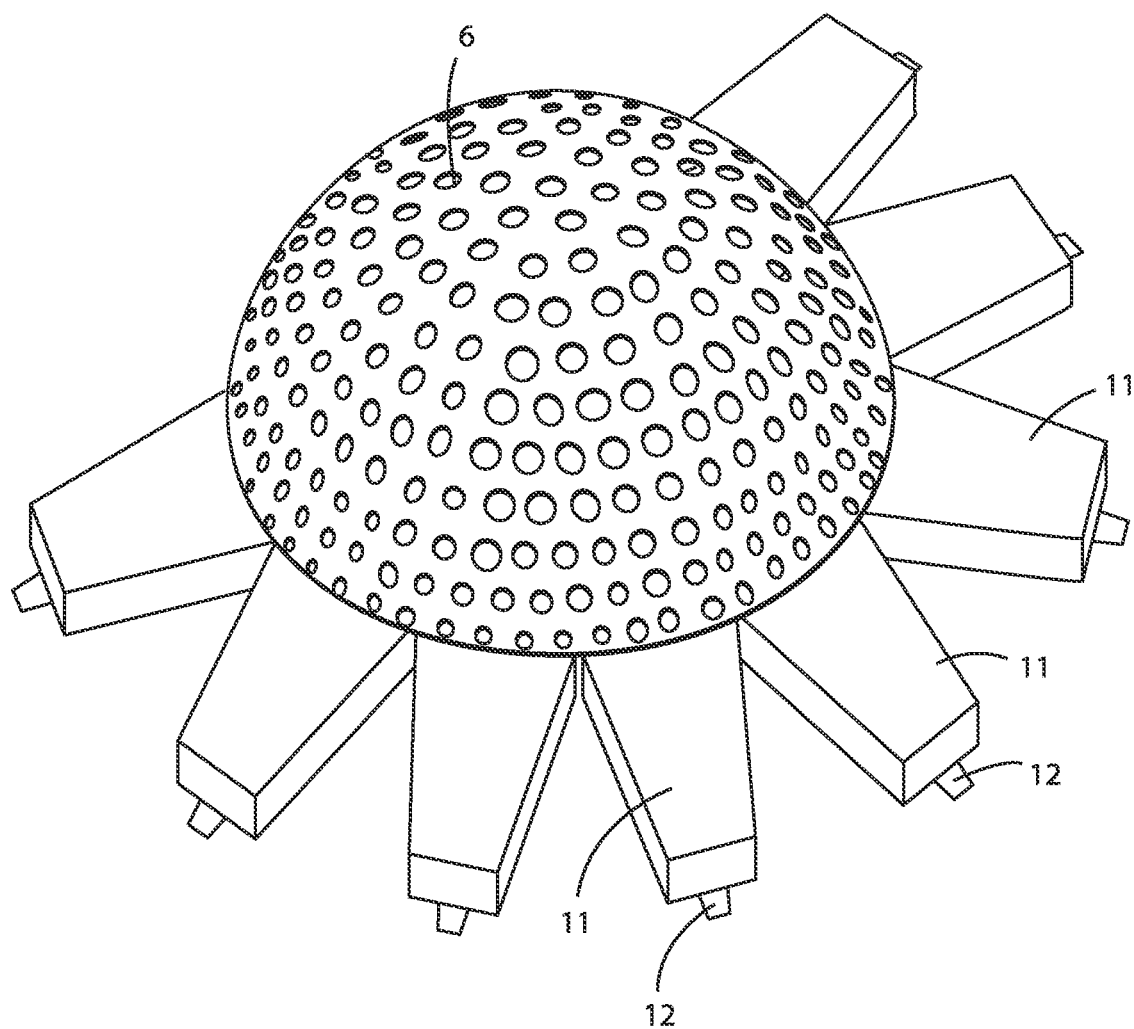
FIG. 9 is a perspective view of a mould and counter-mould.

As is seen clearly in FIG. 4, once the teeth or petals 4 are folded on the rear wall of the prosthesis 1, a disk 5 is applied, which is for example made of smooth or corrugated elastomeric material, covered with polyurethane or made of collagen or another medical grade biopolymer, that covers an area of the teeth 4.

Said disk 5 is applied by gluing, vulcanization or self-vulcanization or by other radio-frequency induction welding methods or use of laser.

Now observing FIGS. 5-8 of the drawings, a preferred proceeding is illustrated for making the covering 2 according to the invention.

In particular, a shell 6 and a counter shell 7 are shown, which are realized for example with resin or by a 3D printer loaded with wire, said wire being realized by certified material for food and pharmaceutical use following a scan of the specific prosthesis 1 to which the covering 2 has to be applied In this manner, each definitive prosthesis 1 model or size will have, in terms of dimensions and shape, a corresponding precise cover that is such as to ensure maximum consistency between the cover and the elastomeric implant, for any size.

Figure 3:
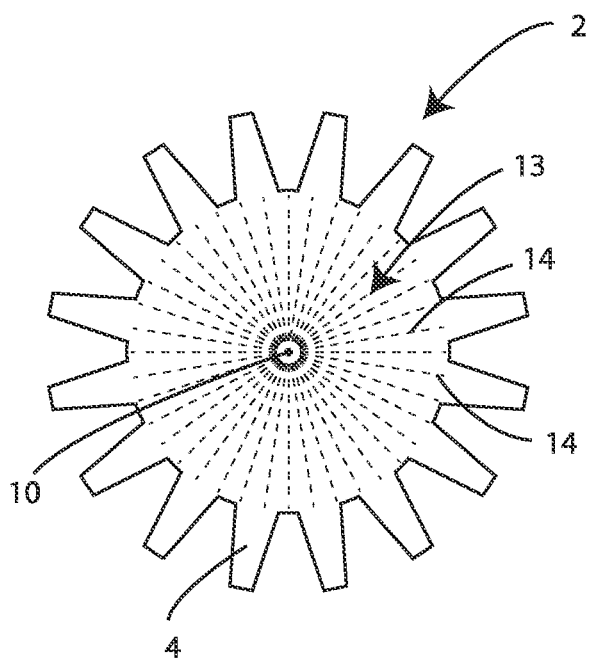
FIG. 3 is a plan view of the covering according to the invention in a first embodiment.
Figure 10:
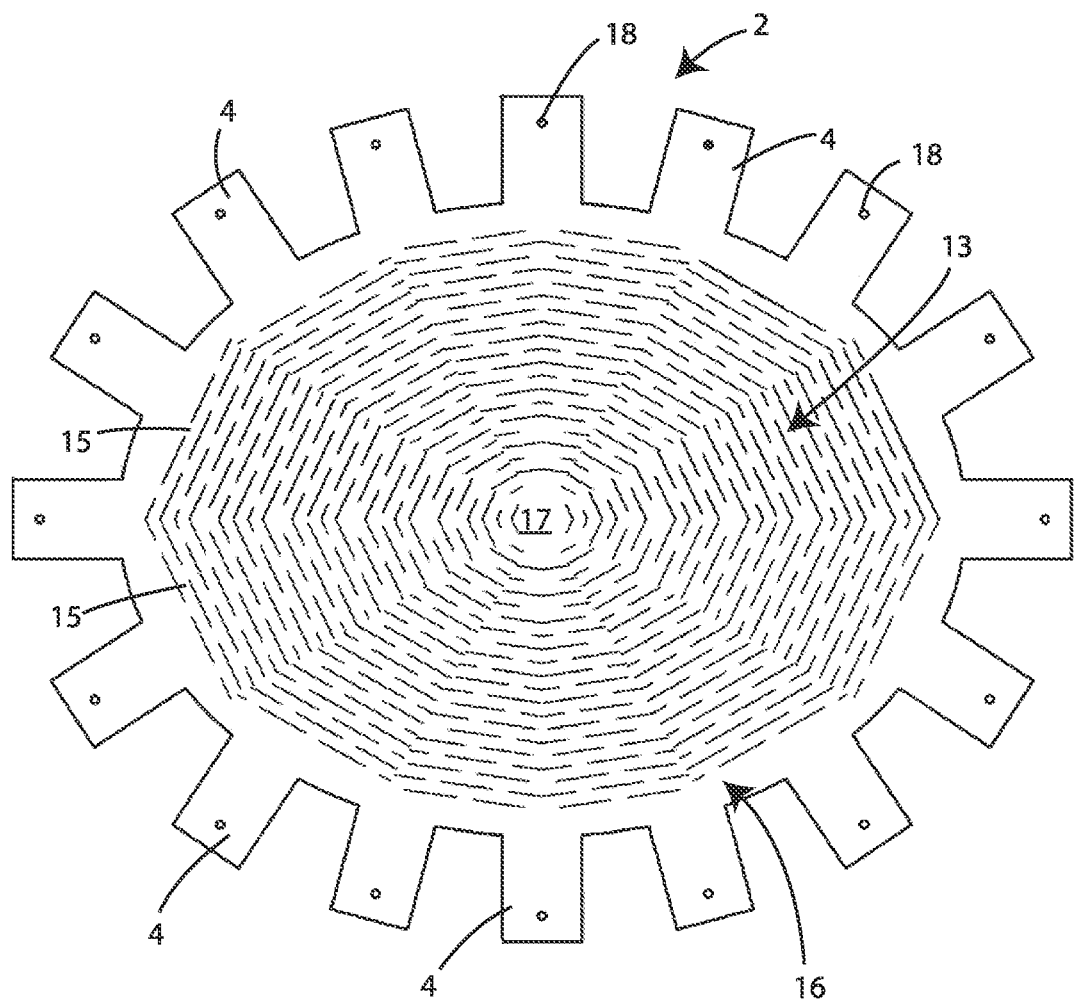
FIG. 10 is a plan view of the covering according to the invention in a second embodiment.

As mentioned, two shells 6, 7 are provided, preferably perforated, wherein before a drying step, for example and preferably by lyophilization, matrices or membranes are applied on said shells 6, 7 in a compact form or in a modified form with a characteristic "mesh" appearance of the covering 2, as for example shown in FIGS. 3 and 10.

The membrane 8, for example made of collagen, which constitutes the covering 2 according to the invention is die-cut to measure and preferably with a centrifugal expansion mesh cut and provided with teeth or fins 4, that will be folded below the prosthesis 1, possibly at the housings 3. Further, the membrane 8 can be cut before lyophilization to obtain the mesh with centrifugal expansion and be die-cut after drying to give the final shape. It can be provided at the outset with teeth or fins 4 or have another geometric shape (rectangular, circular, oval, polygonal).

In the present invention a membrane is a sheet of biological or biosynthetic tissue.

The shell 6 has a centring device 9, that passes through a small hole 10 arranged centrally on the membrane 8, and allows centring thereof in the forming and lyophilization shell 6.

The shell 6 can be provided with fins 11, of a measurement and number equal to those that are possibly present on the membrane 8, provided with hooks 12, which hook the membrane 8 which is preferably made of collagen.

The shell 6, as said, is provided with a centring device 9, to be aligned with the centring hole 10 present on the membrane 8.

The hydrated membrane 8, for example after being rehydrated, is hooked the shell 6, being in this step foldable and extremely drapable, and thus perfectly adaptable to the shell 6. The membrane 8 will have an excess with respect to the profile of the shell 6, to make the aforesaid teeth or petals 4.

The membrane 8, if it has teeth or petals 4, is hooked with the fins 11 by hooks 12, or is hooked with the shell 6 in another manner.

Then the counter shell 7 is inserted inside the shell 6 in order to obtain the definitive shape. In particular, the counter shell 7 is inserted inside the shell 6, against the membrane 8, in order to obtain a pre-shaped membrane 8.

Drying then takes place, preferably in a freeze dryer, for a controlled dehydrating process that enables a preformed shell to be obtained having a measurement and profile that is completely consistent with the prosthesis 1 that it is intended to house.

In this manner, standardized membrane 8 formats can be worked to obtain multiple covers that are different from one another in shape and dimensions, starting from fabrics of a similar measurement, especially in the case of "mesh" coverings.

When the silicone prosthesis 1 is inserted inside the shell 6, the "petals" 4 close towards the centre of the rear face of the prosthesis 1; then superimpose a disk 5 made of smooth or corrugated silicone, covered with polyurethane or collagen or another biopolymer that will, as said, be glued to ensure the junction between the covering and elastomer, blocking the petals of the matrix or of the covering 2.

Sterilization then takes place, which is to be performed with a system that is suitable for not interfering with the physical and molecular structure of the collagen (preferably beta or gamma rays, nevertheless, in some cases, the ethylene oxide, dry heat or hydrogen peroxide plasma sterilization method can be provided).

A prosthesis is thus obtained wherein the two elements, which are perfectly solidly constrained, constitute one body, which allows the surgeon an easy implant, avoids any risky handling and is ready for use.

As shown in FIGS. 3 and 10 the covering 2 according to the invention can have a different shape of the outer perimeter and/or a different configuration of the notches or holes or slits or incisions or cut-outs that make up the mesh portion 13 of the covering 2.

In the context of the present invention, a mesh portion 13 is a surface portion having an alternation of full and empty parts having the aim of confining an object, for example a prosthesis, and having a flexible behaviour, which is able to adapt to the shape of the object to be confined. In particular, the mesh portion 13 is so configured that when the covering 2 is applied to a prosthesis 1, this mesh portion 13 expands and adapts to the outer surface and to the shape of the prosthesis 1.

Preferably, this mesh portion 13 has a centrifugal extension that is such as to adapt in an excellent manner to the shape of the prosthesis 1.

Further, the mesh portion 13 is preferably arranged at the central part of the covering 2.

This mesh portion 13 can be obtained by a mesh of wire-shaped elements, that can be wider at some points and narrower at others, or, as in the case of the disclosed embodiments, in a uniform surface of a substantially two-dimensional thin membrane or sheet, for example made of biosynthetic or biological material, in particular of collagen, which has a plurality of notches that enable the covering obtained to have a three-dimensional behaviour, adapting to the shape of the object to be wrapped.

With reference to FIG. 3, a first embodiment of the covering 1 according to the invention is observed that has a circular shape of the outer perimeter to adapt to a prosthesis 1 of circular shape.

Further, in this embodiment the mesh portion 13 has a plurality of linear notches 14 spaced apart from one another and arranged in spoke fashion.

In the embodiment of FIG. 10, the outer perimeter of the covering 2 has an elliptic shape so as to adapt flexibly both to semi-spherical shapes and to drop shapes of anatomical type of a prosthesis 1, which shapes may also be available on the market.

In fact, this embodiment is advantageously able to easily cover different solids homogeneously and without interruption between the covering and the substrate.

Preferably, the proportional ratio between the axes of the ellipse is 2:1.6, inasmuch as it enables most commercially available breast prostheses with a round or oval base to be covered.

Nevertheless, the proportional ratio between the axes can have different proportional ratios starting from 1:1, which defines a round base, up to 3:1.

In other embodiments the perimeter of the covering can also have a polygonal shape, preferably a polygonal shape that can be circumscribed or inscribed in a circle or an ellipse.

As for the preceding embodiment, the mesh portion 13 has a plurality of radial notches 15 that allow centrifugal expansion of the membrane for wrapping prostheses of various measurements and shapes (round, anatomical, etc).

In particular, such radial notches 15 are obtained spaced apart from one another on concentric closed lines. In particular, these concentric closed lines can be closed ellipses, circles or polygons.

In the embodiment in question, such radial notches 15 are arranged on concentric polygons on the basis of a characteristic section structure, i.e. arranged in areas converging towards the centre, of triangular shape. In particular, said notches 15 are so arranged as to form a plurality of triangular, adjacent and contiguous sections. In order to optimize expansion aptitude without penalizing the ability to cover consistently as much surface as possible, a closed polygon is preferred with twelve sides or twelve sections, which nevertheless, in other embodiments, can vary from a minimum of two to a maximum of forty-eight sections.

In particular, in the case of a covering 2 of circular shape these polygons can have equal angles.

Said notches 15 in said mesh portion 13 can take on the appearance of small non-continuous cuts, aligned in alternating rows, but also the appearance of notches having a spiral appearance, which are aligned towards the centre in spoke fashion or another appearance that ensures the possibility of expansion to the biological or biosynthetic membrane.

The length of the notches 14 or 15 can vary from 2 mm to 2 cm both for the preferred form and in the alternative forms (spiral and in spoke fashion), whereas the distance between those aligned can vary from 2 mm to 2 cm. In the case of the arrangement illustrated in FIG. 10, the preferred distance between the rows is 2 mm but can increase up to 2 cm, i.e. up to the point wherein the expandability of the membrane would be substantially compromised. Furthermore, in the case of the arrangement illustrated in FIG. 10, the preferred number of rows is twenty-two, but it may vary as a function of the distance between each row.

In other embodiments, said notches can have a "Y" or "S"-shaped shape.

In particular, according to the invention, said notches 14 are so arranged as to have a centrifugal extension with respect to the centre of said covering 2, allowing homogeneous expansion of the covering, which can cover and adhere perfectly to the prosthesis, in particular of hemispherical shape.

Figure 14:
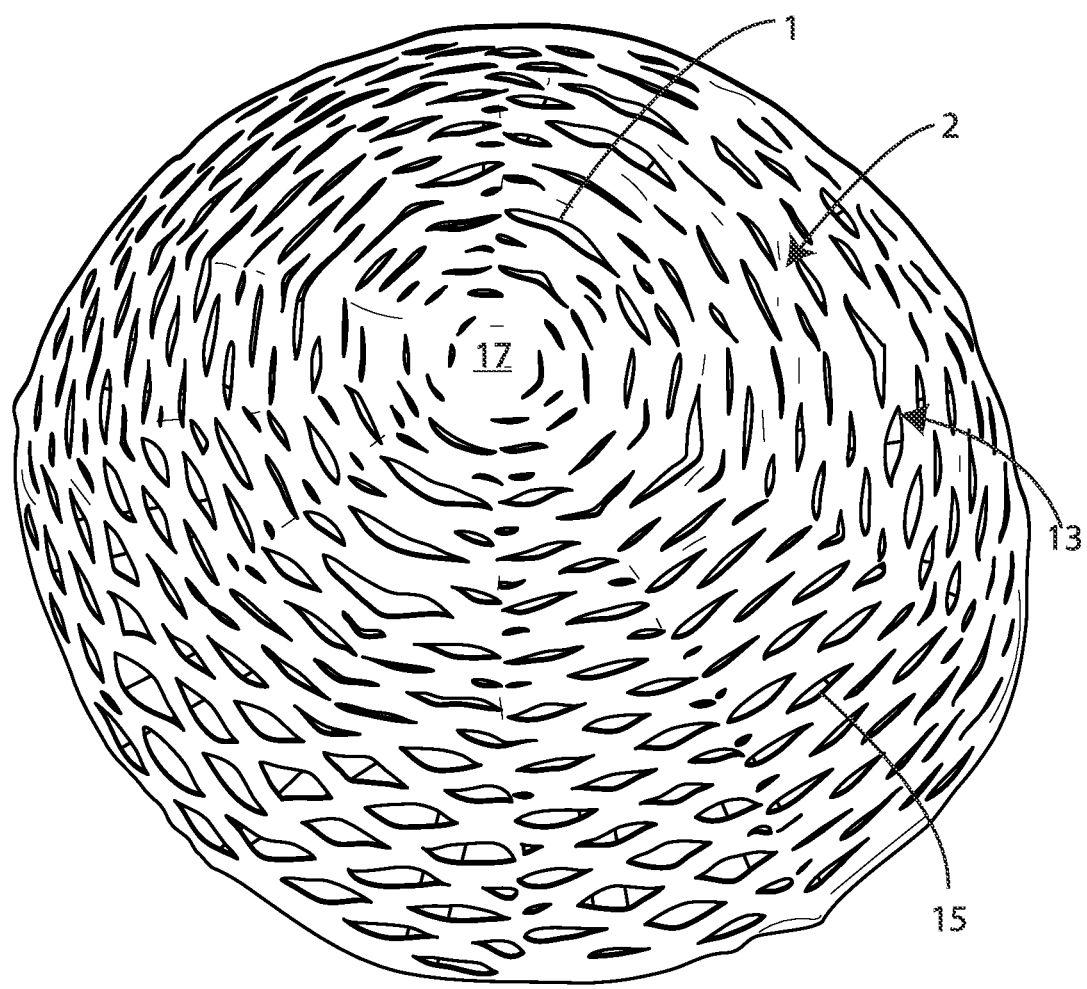
FIG. 14 shows a perspective top view of the covering according to the invention, according to FIG. 10 or 12, that wraps a breast prosthesis.
Figure 17:
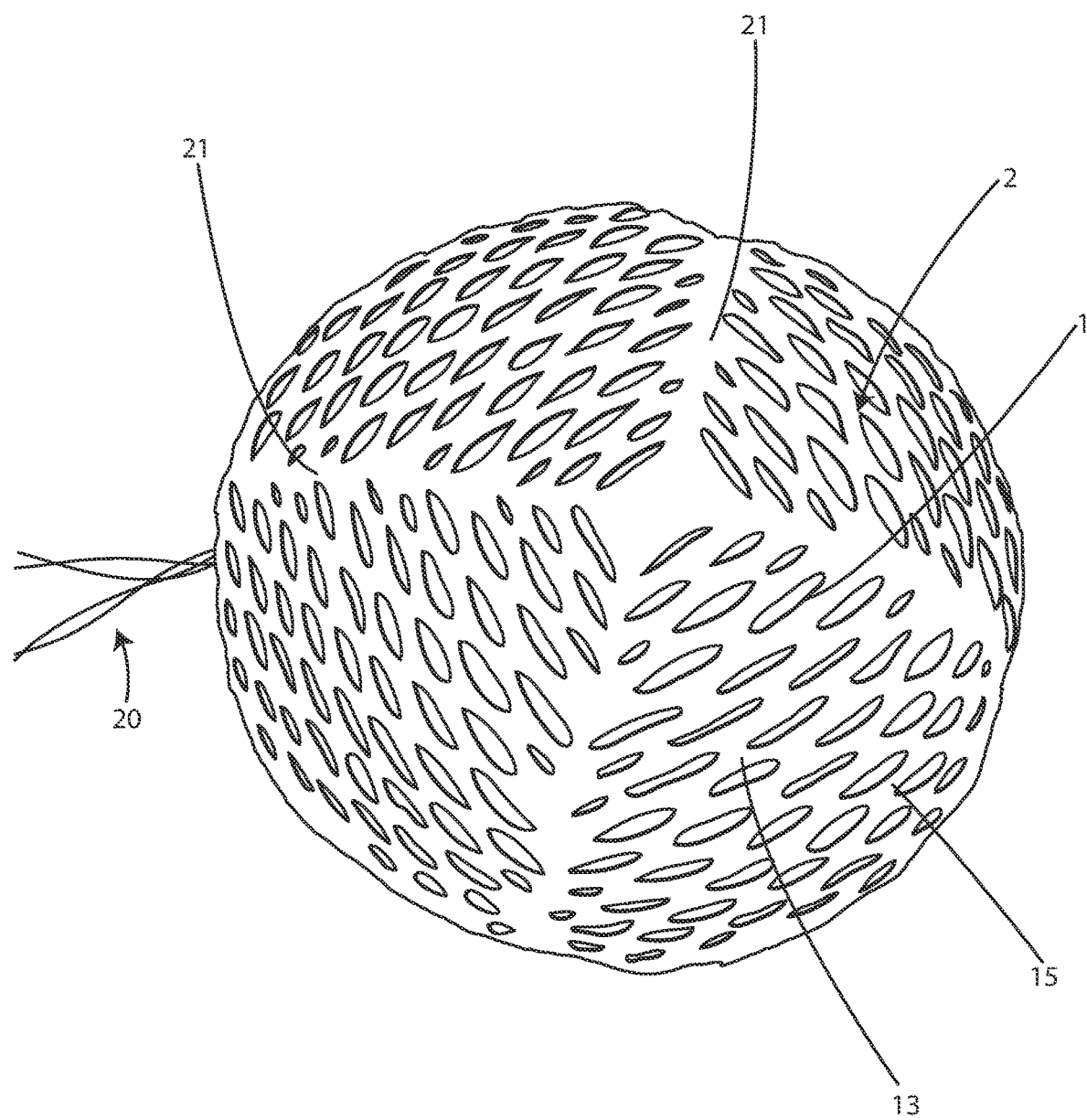
FIG. 17 shows a perspective top view of the covering according to FIG. 16, that wraps a breast prosthesis.

In other words, they are centrifugal slits 15, present homogeneously and regularly over all the covering 2. These notches or slits 15 enable the covering 2 to spread in a three-dimensional direction on the prosthesis 1 (as shown in FIG. 14 or FIG. 17), and are so arranged as to promote protection also in the case of considerably projecting prostheses.

In order to confer optimum load resistance, said covering 2 preferably has a peripheral portion or band 16 with a full non-uniform surface that surrounds on the perimeter the mesh portion 13 and covers, when the covering 2 is applied to a prosthesis 1, the base portion or rear surface of the prosthesis 1.

The peripheral portion 16 is excluded from slitting in order to allow greater resistance to tearing when the covering 2 is applied to, or wrapped around, the prosthesis 1. Further, it enables the cover to be made more homogeneous starting with the base of the prosthesis 1, as at the base of the prosthesis 1 the deformation pressure during handling is concentrated.

If another geometric shape of the perimeter of the covering 2 is opted for, such as for example a circular or polygonal shape, the surface without incisions is anyway arranged along the entire perimeter.

Preferably, the peripheral portion 16 can have a minimum thickness of 5 mm and a maximum thickness of 3 cm in order not to compromise the "draping" capacity of the membrane.

In this context, the thickness of the peripheral portion 16 relates to the radial length between the mesh portion 13 and the outer perimeter of the covering 2.

Further, also the central portion 17 of the covering 1 can preferably have a uniform surface, free of notches or incisions. This central portion 17 is arranged at the centre of the covering 2 and is surrounded by the mesh portion 13.

The central portion 17 has the function of constraining the expansion direction lines of the covering 2 and is typically located above the point of maximum projection of the breast prosthesis 1.

Preferably, the diameter of the central portion 17 can vary from 2 cm to 5 cm, in order to perform its function without adversely affecting the homogeneity of the expansion.

Figure 15:
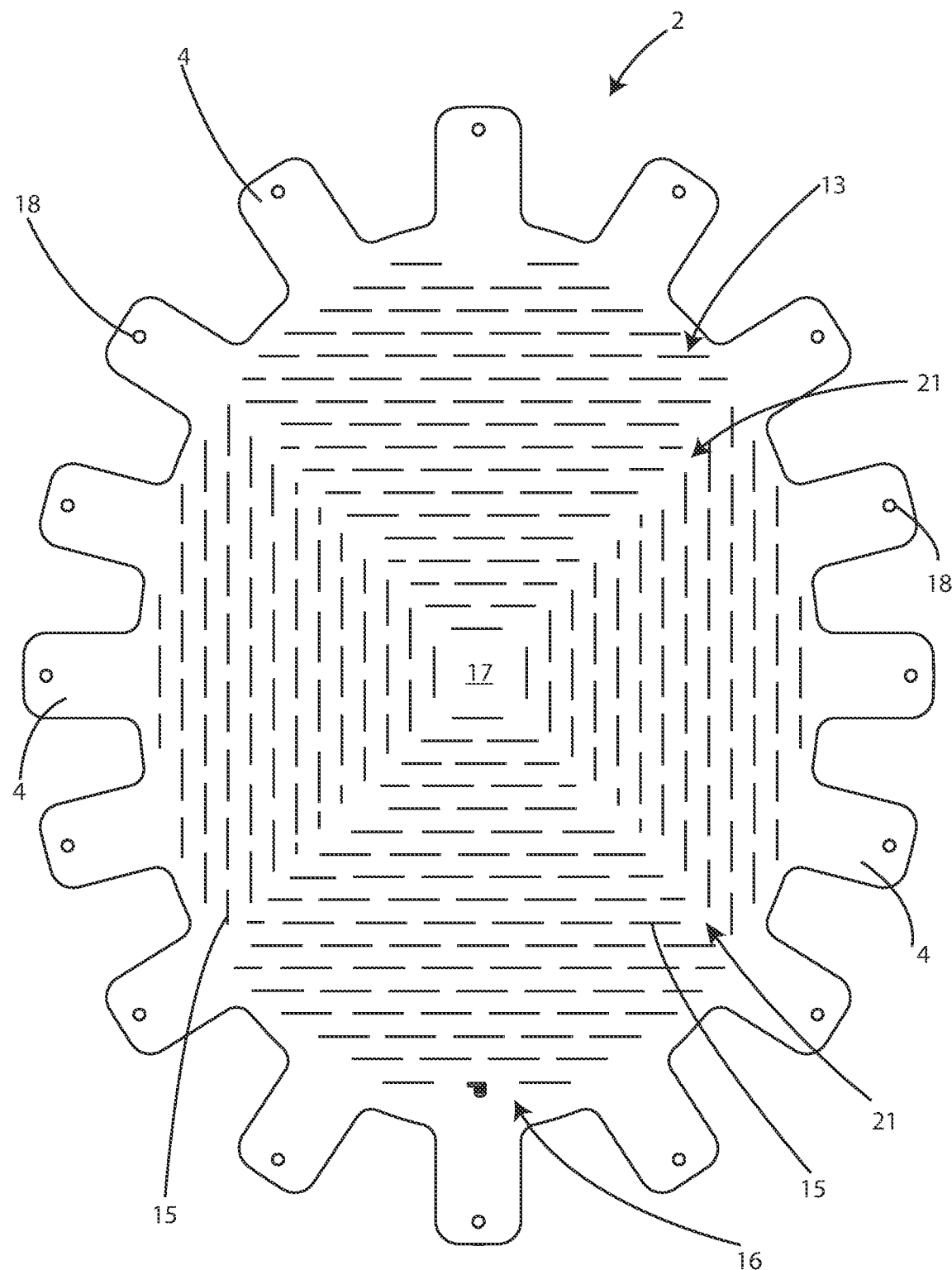
FIG. 15 is a plan view of the covering according to the invention in a fourth embodiment.
Figure 16:
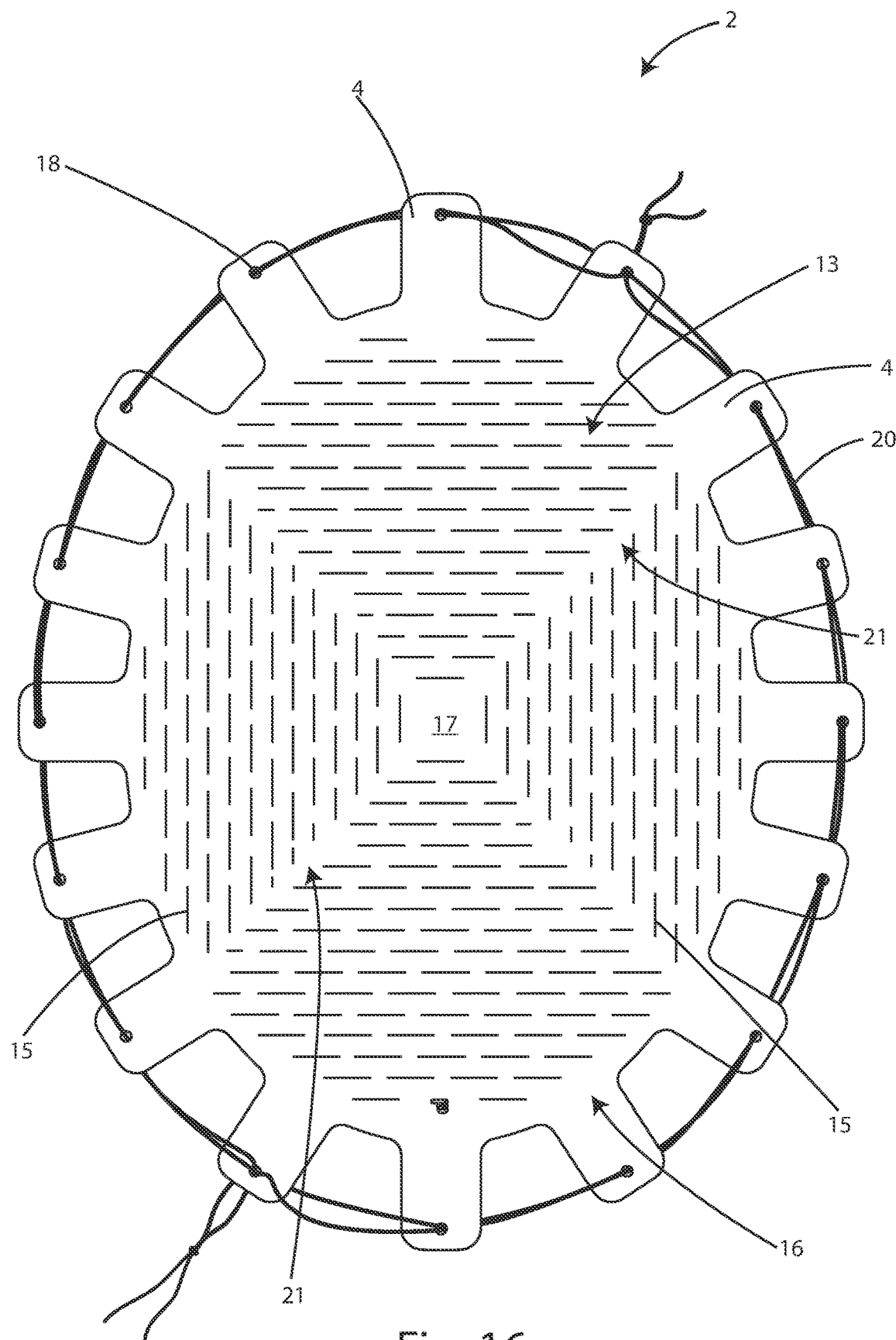
FIG. 16 shows a plan view of the covering of FIG. 15 and two through wires for the holes of said covering so as to obtain "tobacco-bag" clamping.

In a further embodiment, for example as shown in FIGS. 15-17, the sections are adjacent, but there is a uniform area 21 devoid of notches (or any other type of cuts, incisions or slits), between each adjacent section, dividing them. However, in other embodiments, not all the adjacent sections may be divided by a uniform area 21.

Specifically, such uniform areas 21 connect the central portion 17 to the peripheral portion 16 of the covering 2. In particular, each uniform area 21 is arranged in spoke fashion, with respect to the centre of said covering 2, extending along a radius of said covering 2.

The presence of such uniform areas 21 increases the resistance of said covering 2. In fact, when the covering 2 is applied on a prosthesis 1, the uniform areas 21 form reinforcement ribs of said covering 2 (as shown in FIG. 17).

In the embodiment shown in FIGS. 15-17, said covering 2 has four sections and four corresponding uniform areas 21 dividing the adjacent sections. Such arrangement allows to achieve a reinforced covering 2 with a good extensibility of the mesh portion 13, compared to embodiments with a greater number of uniform areas 21. However, different divisions may be possible, the number of sections and uniform areas being preferably between three and six.

Furthermore, in the embodiment shown in FIGS. 15-17, the preferred distance between each row of notches 15 is greater than the preferred distance used in the other embodiments described, e.g. being around 3 mm, to reduce the risk of rupture of the covering 2. In fact, the preferred number of rows of said notches 15 is seventeen, in order to obtain a greater resistance to being teared apart, if compared with other embodiments. However, other distances/number of rows may be used.

In addition, in such embodiment, said notches 15 in said mesh portion 13 are arranged on concentric rectangular shapes. However, other arrangements are possible.

Furthermore, in such embodiment, the central portion 17 has also a substantially squared-shape, being grater in size than the central portions 17 of the embodiments with a rounded shape.

Finally, in the embodiment shown in FIGS. 15-17 a reference sign, in particular a letter "P", is added close to the peripheral portion 16, so as to identify the face of the covering 2, which has to contact the prosthesis 1. However, such sign may be omitted in other embodiments and/or may be used also in embodiments without said uniform areas 21.

As said previously, the covering 2 according to the invention has a plurality of petals or teeth 4 at the outer crown of the covering 2 that, in the preferred configuration, are sixteen in number but can vary from a minimum of two to a maximum of forty-eight.

In particular, said petals or fins 4 are arranged in spoke fashion on the outer perimeter of said covering 2. In other words, said petals or fins 4 are arranged radially on the outer perimeter of said covering 2, with respect to the central portion 17 of said covering 2. More in particular, they are distributed so as to be substantially equidistant.

In the embodiment of FIG. 10, said petals 4 are 20 mm in length to allow the best approximation of the edges of the closing covering 2 without becoming superimposed. Nevertheless, on the basis of the chosen shape and dimension, this length can vary between 5 and 50 mm.

The profile of the petals 4 can be sharp-edged or squared or rounded, in other words show a characteristic arc shape that enables the possibility to be advantageously avoided of folding on itself of the apexes of the petal 4.

As an alternative method of coupling the covering 2 according to the invention with a prosthesis 1 with respect to what has been disclosed previously, the covering 2 can provide a through hole 18 (as shown for the embodiment of FIG. 10) obtained on each petal 4 or on some petals 4. Said holes 18 enable at least one wire or thread 20 to pass through, in particular a wire for stitching or stitching wire or suture thread, such that, when the covering 2 wraps a prosthesis 1, pulling the ends of the through wire 20 passing through said holes 18, the petals 4 clamp or tighten on one another and thus the margins of the covering 2 around the base or rear surface of the prosthesis 1 to be covered. In other embodiments, two wires 20 can be used, as shown in FIGS. 12 and 13a and 13b or in FIG. 16.

Wire for stitching or stitching wire or suture threads are wires or threads made of medical material that are commonly used during surgical operations and can be of the type that is resorbable by the organism. In the context of the present invention, the wire is never stitched either to the prosthesis or to the muscle or to the edge, so the stitching wire is not used in combination with a needle, but the stitching definition thereof is linked to the category of wires of medical type, which are preferably resorbable.

Figure 12:
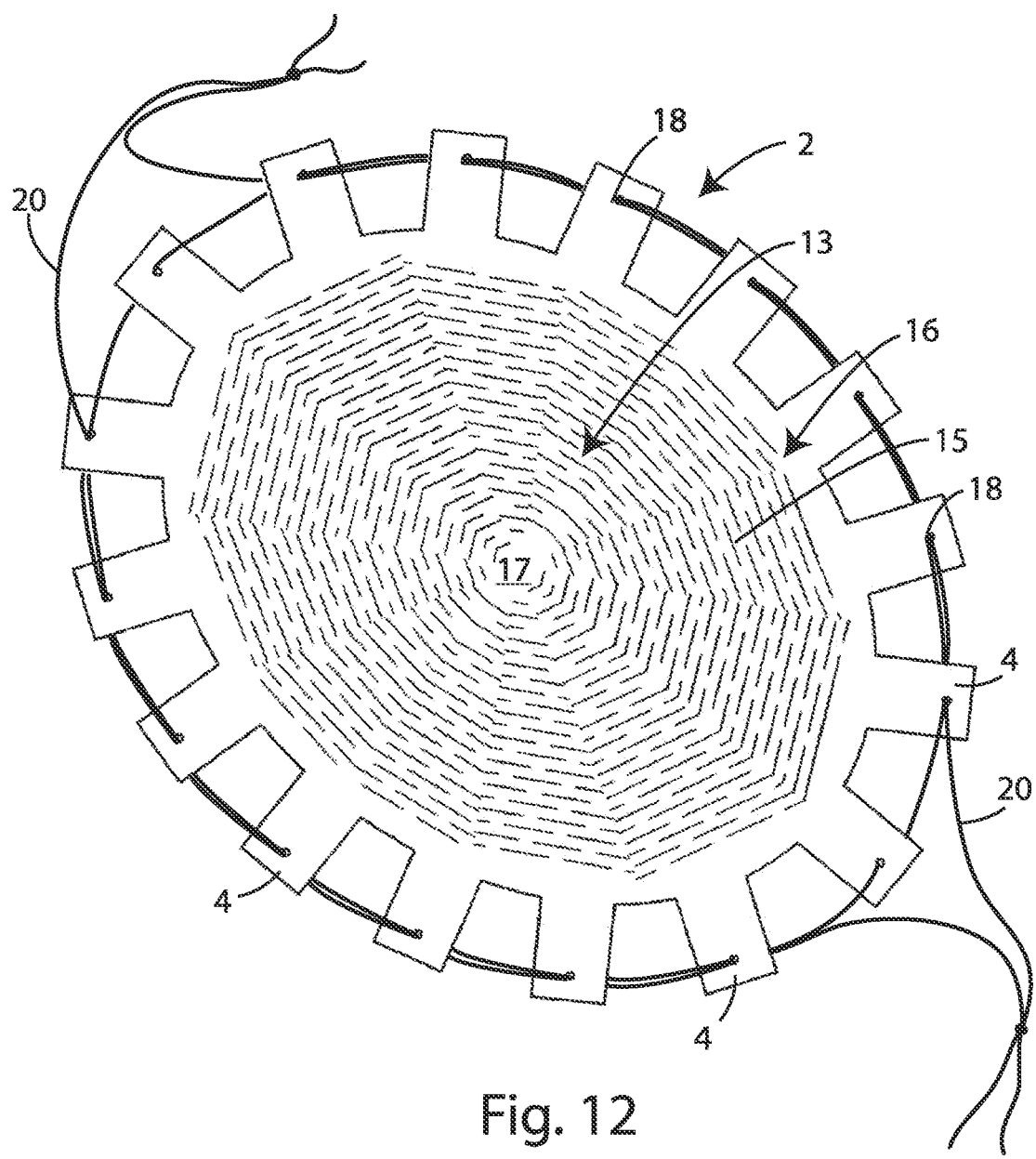
FIG. 12 shows a plan view of the covering of FIG. 10 and two through wires for the holes of said covering so as to obtain "tobacco bag" clamping.
Figure 13A:
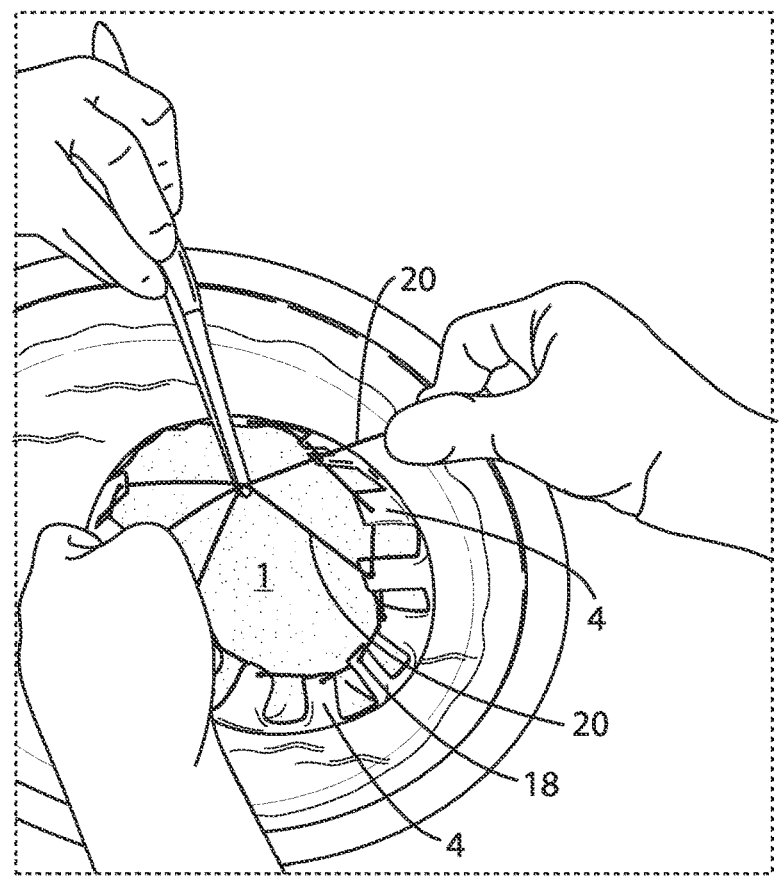
FIGS. 13a and 13b show respectively two perspective views of two closing steps of the covering of FIG. 12 by the wires to obtain "tobacco bag" clamping.
Figure 13B:
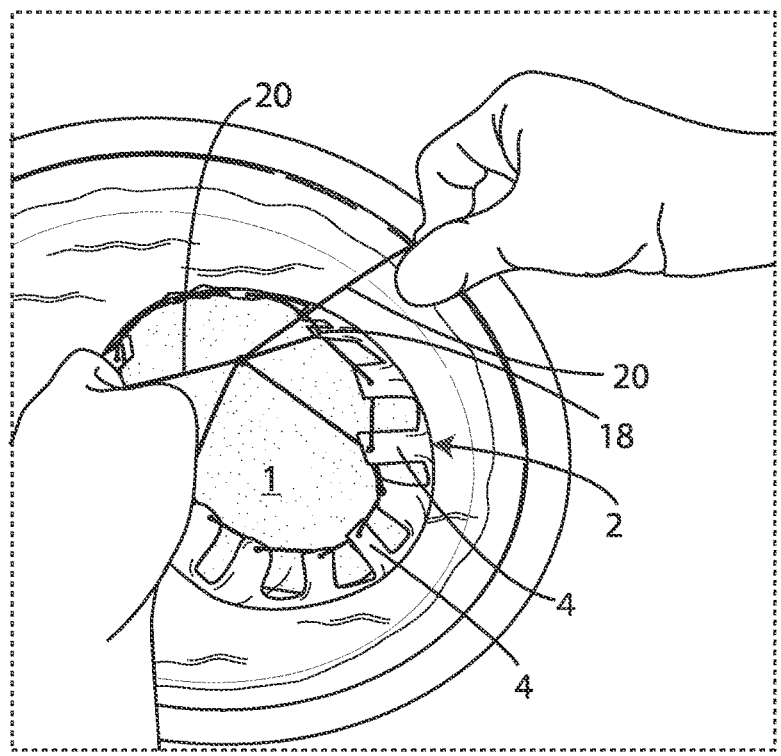

In particular, as shown in FIGS. 12, 13a and 13b or in FIG. 16, the two wires 20 can be arranged and pass through said holes 18 or slots of the covering 1 so as to make a "tobacco bag" closure also so-called "purse-string" closure.

In particular, each wire 20 makes a semi-complete rotation around the covering 2 so as to join the ends at opposite sides of the covering 2.

Accordingly, once the covering 2 is applied to a prosthesis 1 at the front surface thereof, pulling the two end pairs of the two wires 20 at the rear surface thereof (as shown in FIGS. 13a and 13b), clamping or tightening of the petals or fins 4 on the rear portion of the prosthesis 1 is obtained. This solution enables the covering 2 to be applied easily and fast to a prosthesis 1 also directly in the operating theatre before the surgical operation, reducing application times thereof.

Further, this enables the matrix or prosthesis to be handled very little, decreasing the possibility of contamination thereof.

In fact, as shown in figures, the surgeon or the operator can mainly handle the prosthesis 1-covering 2 assembly by the wires 20, which the surgeon or the operator links together through the use of specific grippers.

The prosthesis-covering assembly can be handled in a fluid, in particular a liquid, for example physiological solution, to rehydrate the membrane of the covering 2, if in dehydrated form.

In particular, the method will be disclosed below for applying the covering 2 of FIGS. 10-13 to a prosthesis.

The covering 2 is extracted with a sterile procedure from the package, in particular a double blister. If it is made of a dehydrated membrane it is rested inside a bowl containing a fluid, in particular physiological solution preferably at ambient temperature, both of which are sterile.

There is a short wait, in particular of about ten minutes, so that if the covering is made of dehydrated membrane it is rehydrated and returns to being soft and "drapable".

If the membrane is made of bi-layer pericardium, the measure will be used of making the fibrous side of the pericardium face the bottom of the bowl, keeping the compact side visible that is intended to receive the breast prosthesis. In the case of a dermis or non bi-layer pericardium, this measure is not necessary.

Subsequently, the prosthesis 1 is applied to the covering 2, resting the front portion of the prosthesis 1 at the mesh portion 13.

By simultaneous traction of the two opposite heads of the perimeter double wire 20 (so that each wire arranged along the perimeter exits with both the heads) the petals 4 cover part of the rear portion of the prosthesis 1, approaching closer to the centre the more decisive the traction on the wires 20 becomes. This is particularly visible from FIGS. 13a and 13b, where the rear surface of the prosthesis 1 is seen that is wrapped by the fins 4 that are clamped or tightened and fixed by the wires 20.

When the assembled prosthesis-covering is complete the four heads of the wires 20 are knotted to ensure a complete cover of the front surface.

As can be seen from FIG. 14 or FIG. 17, the covering 2 according to the invention adheres optimally to the surface of the prosthesis 1.

This enables the covering to be fixed perfectly to the prosthesis, so as to induce neovascularization of the covering in contact with the tissues of the organism, becoming integrated with the tissues.

Advantageously, as the wires 20 pass through all the petals or fins 4 or through a good part thereof, if a petal or fin 4 were to be broken inadvertently, the covering 2 would remain advantageously adhering to the prosthesis 1, owing to the remaining petals or fins 4 clamped by said one or more wires 20.

In other words, said pair of wires 20 are arranged on the perimeter of the covering 2 and inserted in an opposite direction to one another through holes 18 (for example eyelets or slots) located at the final portion of extensions in the shape of petals 4 made on the outer margin of the biological or synthetic resorbable covering 2.

Said wires 20, simultaneously subjected to manual traction, determine the synchronous approach of the petals 4 to the centre of the rear face of the prosthesis 1 and consequently wrapping of the prosthesis 1 by the covering 2, on the model of a "tobacco bag" closure.

However, in other embodiments, such "tobacco-bag" closure may also be achieved using only one wire 20 arranged on the perimeter of the covering 2 or more wires 20 inserted in the same direction to one another through holes 18.

The covering 2 according to the invention can be marketed in the form of a kit wherein the wire or the wires 20 are already inserted inside said holes 18, or in the intraoperative step the user inserts the wires supplied in a kit or already at the disposal of the user in the specific holes 18 of the covering 2 before applying the covering 2 to the prosthesis 1.

Preferably, each hole 18 is arranged in the upper third of the height of the respective petal 4.

Said hole 18, can be single or double, can be of circular shape with a diameter of 1.5 mm, in each case a measurement that allows easy sliding of the stitching wire without compromising the necessary friction coefficient that allows the manoeuvre of clamping the covering 2 on the prosthesis 1.

In each case, the diameter of the hole 18 can be comprised between 0.5 mm and 3.0 mm.

In other embodiments that are not shown said hole 18 can also be a single or double slot-shaped incision, for example two parallel incisions to form a through hole.

Figure 11:
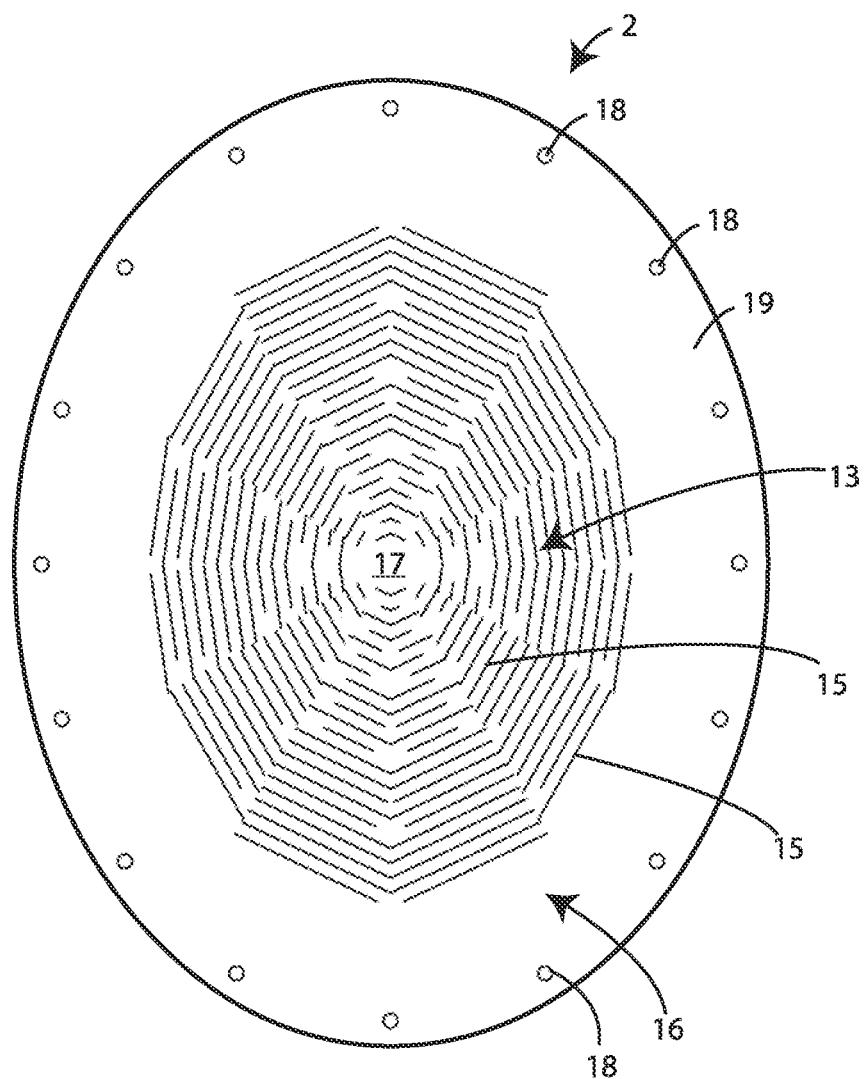
FIG. 11 is a plan view of the covering according to the invention in a third embodiment.

In other embodiments, for example as shown in FIG. 11, said covering 2 may have not said plurality of petals or fins but have a single outer perimeter edge 19 at which said plurality of holes 18 is obtained for the passage of one or more wires, in particular stitching wires.

The coupling method of the covering with coupling with a prosthesis is the method disclosed previously.

Advantageously, the covering according to the present invention enables the cutaneous muscular strip or cutaneous muscle to be protected from possible adverse effects caused by the contact with the surface of the prosthesis (in particular inflammatory phenomena).

This is particularly allowed by the covering according to the invention that, by adhering in an optimum manner to the prosthesis, is interposed between a synthetic element, the silicone prosthesis and the tissues of the organism.

Advantageously, the covering according to the invention covers the entire front portion of the prosthesis in order to protect the strip superimposed on the prosthesis.

In fact, the covering according to the invention protects the critical interface, which is the contact portion between the front surface of the prosthesis and the tissue strip; the petals, in the rear portion, help to achieve clamping of the covering on the prosthesis. This advantageously allows the use of biological or biosynthetic material, using the material only where needed, without an excess of biological mass implanted (for example in the rear portion).

Also advantageously, the covering according to the invention does not involve the use of adhesives.

Still more advantageously, the covering according to the invention is secure in the sense that it seals very firmly on the prosthesis, is non-invasive, simple and rapid to apply.

Further, the covering according to the invention does not require the use of any stitching points on the tissues and is thus minimally invasive. Inter alia, not even the covering has to be sown or stitched on itself.

Further, one advantage of the covering according to the invention is that it is usable and compatible with all prostheses, in particular breast prostheses, present on the market, being virtually universal.

Also, the covering according to the invention enables contamination to be reduced owing to the extremely reduced handling during the intraoperative step, in particular it requires less than 5 minutes for applying the covering to any prosthesis.

The present invention has been described for non-limiting illustrative purposes, according to its preferred embodiments, but it is to be considered that any variations and/or modifications may be made by experts in the field without departing from the relative scope of protection, as defined by the appended claims.

What is claimed is:

1. A covering (2) for a prosthesis (1), said prosthesis (1) having a rear surface which, when applied, is faced towards the person on whom the prosthesis (1) is applied, said covering (2) having a fixing system (4; 3) to said prosthesis (1), said fixing system providing a plurality of teeth or petals (4), realized on said covering (2), said teeth or petals (4) being so configured as to be foldable, so that when the covering (2) is arranged on said prosthesis (1) said teeth or petals (4) are coupled with said rear surface of the prosthesis (1), by securing means (5) for securing the teeth or petals (4) folded over said prosthesis (2), wherein on at least two or on each tooth or petal (4) a through hole (18) or at least one slot-shaped incision, for example single or double, is obtained, said through hole (18) or at least one slot-shaped incision being adapted to the passage of at least one thread, in particular at least one suture thread.

2. The covering (2) according to claim 1, wherein said plurality of teeth or petals (4) are between two and forty-eight.

3. The covering (2) according to claim 1, wherein said plurality of teeth or petals (4) are arranged in spoke fashion on the outer perimeter of said covering (2).

4. The covering (2) according to claim 1, wherein said plurality of teeth or petals (4) have a length comprised between 5 mm and 50 mm.

5. The covering (2) according to claim 1, wherein each through hole (18) or incision is arranged in the upper third of the height of the respective tooth or petal (4).

6. The covering (2) according to claim 1, wherein the diameter of each hole (18) is comprised between 0.5 mm and 3.0 mm.

7. The covering (2) according to claim 1, wherein the covering (2) has a mesh portion (13), in particular at a central part of said covering (2).

8. The covering (2) according to claim 7, wherein said mesh portion (13) has a centrifugal expansion.

9. The covering (2) according to claim 1, wherein the outer perimeter of said covering (2) has a circular or elliptic or polygonal shape or polygonal shape adapted to be inscribed or circumscribed in a circle or an ellipse.

10. The covering (2) according to claim 9, wherein when the outer perimeter of the covering (2) has an elliptic or circle shape, the proportional ratio between the axes of the ellipse is comprised between 1:1 to 3:1.

11. The covering (2) according claim 1, wherein covering (2) is made exclusively from one or more biopolymers or from a mixture of one or more biopolymers and further ingredients, such as for example elastin.

12. The covering (2) according to claim 1, wherein covering (2) is made of resorbable and biocompatible material.

13. The kit for covering a prosthesis (1), said kit comprising a covering (2) according to claim 1, wherein the kit comprises one or more threads for fixing said covering (2) to said prosthesis (1), wherein said one or more threads are adapted to pass through said holes (18) or incisions obtained on said teeth or petals (4) or on said perimeter edge (19) of said covering (2).

14. The kit according to claim 13, wherein said one or more threads (20) are inserted through said holes (18) or incisions.

15. The kit according to claim 14, wherein said one or more threads (20) are inserted through said holes (18) or incisions so that, when said covering (2) is in use for covering a prosthesis (1), and said one or more threads (20) are subjected to manual traction, said teeth or petals (4) are synchronously pulled towards the centre of the rear face of the prosthesis (1), consequently causing the wrapping of the prosthesis (1) by the covering (2).

16. The kit according to claim 14, wherein the kit comprises a pair of threads (20) inserted through said holes (18) in an opposite direction to one another, so that their respective ends are coupled on opposite sides of the covering (2).

17. The kit for covering a prosthesis (1), wherein said kit comprising a covering according to claim 1, and a breast prosthesis (1) having a rear surface, said covering (2) being applied on said breast prosthesis (1) with said plurality of teeth or petals (4) folded and fixed at said rear surface.

18. A covering (2) for a prosthesis (1), said prosthesis (1) having a rear surface which, when applied, is faced towards the person on whom the prosthesis (1) is applied, said coveting (2) having a fixing system (4; 3) to said prosthesis (1), said fixing system providing a plurality of teeth or petals (4), realized on said covering (2) said teeth or petals (4) being so configured as to be foldable, so that when the covering (2) is arranged on said prosthesis (1) said teeth or petals (4) are coupled with said rear surface of the prosthesis (1), by securing means (5) for securing the teeth or petals (4) folded over said prosthesis (2), wherein the covering (2) has a mesh portion (13), in particular at a central part of said covering (2), wherein the mesh portion (13) has a plurality of notches (14, 15).

19. The covering (2) according to claim 18, wherein said notches (14) have a centrifugal expansion with respect to the centre of said covering (2).

20. The covering (2) according to claim 18, wherein said notches (15) are radial notches (15), arranged on closed concentric or spiral lines.

21. The covering according to claim 20, wherein said closed lines have a polygonal shape.

22. The covering (2) according to claim 18, wherein said notches (5) are so arranged as to form a plurality of adjacent and contiguous triangular sections.

23. The covering (2) according to claim 18, wherein said notches (15) are so arranged as to form a plurality of adjacent triangular sections separated by a uniform area (21), wherein each uniform area (21) is devoid of notches or cuts or incisions or slits, and connects a central portion (17) to a peripheral portion (16) of the covering (2).

24. The covering (2) according to claim 23, wherein said triangular sections are between three and six triangular sections.

25. The covering (2) according to claim 18, wherein the length of each of said notches (14, 15) is comprised between 2 mm and 2 cm.

26. The covering (2) according to claim 20, wherein the distance between several closed lines is comprised between 2 mm and 2 cm.

27. A kit for covering a prosthesis (1), said kit comprising a covering (2) according to claim 18, wherein the kit comprises a disk (5) for fixing said covering (2) to said prosthesis (1), wherein said disk (5), said disk (5) being so configured that when said covering (2) is arranged on said prosthesis (1), said disk (5) is able to cover an area of the teeth or petals (4).

28. The kit for covering a prosthesis (1) according to claim 27, wherein said disk (5) is made of smooth or corrugated elastomeric material, covered with polyurethane, or of collagen or of another medical grade biopolymer.

29. A covering (2) for a prosthesis (1), said prosthesis (1) having a rear surface which, when applied, is faced towards the person on whom the prosthesis (1) is applied, said covering (2) having a fixing system (4; 3) to said prosthesis (1), said fixing system providing a plurality of teeth or petals (4), realized on said covering (2), said teeth or petals (4) being so configured as to be foldable, so that when the covering (2) is arranged on said prosthesis (1) said teeth or petals (4) are coupled with said rear surface of the prosthesis (1), by securing means (5) for securing the teeth or petals (4) folded over said prosthesis (2), wherein the covering (2) has a mesh portion (13), in particular at a central part of said covering (2), wherein said covering (2) has a peripheral portion or band (16) made of a full non uniform surface that surrounds peripherally the mesh portion (13), said peripheral band (16) being devoid of notches or incisions or slits.

30. The covering (2) according to claim 29, wherein said peripheral band (16) has a thickness comprised between 6 mm and 3 cm.

31. A covering (2) for a prosthesis (1), said prosthesis (1) having a rear surface which, when applied, is faced towards the person on whom the prosthesis (1) is applied, said covering (2) having a fixing system (4; 3) to said prosthesis (1), said fixing system providing a plurality of teeth or petals (4), realized on said covering (2), said teeth or petals (4) being: so configured as to be foldable, so that when the covering (2) is arranged on said prosthesis (1) said teeth or petals (4) are coupled with said rear surface of the prosthesis (1), by securing means (5) for securing the teeth or petals (4) folded over said prosthesis (2), wherein the covering (2) has a mesh portion (13), in particular at a central part of said covering (2), wherein the covering (2) provides a central portion (17) surrounded by said mesh portion (13), said central portion (17) having a uniform surface devoid of cuts or incisions or slits.

32. The covering (2) according to claim 31, wherein the diameter of said central portion (17) varies between 2 cm and 5 cm.

* * * * *

UNITED STATES PATENT AND TRADEMARK OFFICE
CERTIFICATE OF CORRECTION

PATENT NO. : 12,004,942 B2
APPLICATION NO. : 17/019424
DATED : June 11, 2024
INVENTOR(S) : Flavio Nanni et al.

It is certified that error appears in the above-identified patent and that said Letters Patent is hereby corrected as shown below:

On the Title Page

In item (73) Assignee, Line 2:
"Federia" should be changed to -- Federica --

Insert the following:
Item (30) Foreign Application Priority Data:
-- Mar 13, 2018 (IT)......................102018000003509
Oct 26, 2018 (IT)......................102018000009810 --

Signed and Sealed this
Twelfth Day of November, 2024

Katherine Kelly Vidal
*Director of the United States Patent and Trademark Office*